United States Patent [19]

Petronella

[11] 4,438,038

[45] Mar. 20, 1984

[54] PROCESS FOR THE PRODUCTION OF OIL-SOLUBLE METAL SALTS

[75] Inventor: Joseph Petronella, Old Bridge Township, Middlesex County, N.J.

[73] Assignee: Nuodex Inc., Piscataway, N.J.

[21] Appl. No.: 378,022

[22] Filed: May 13, 1982

Related U.S. Application Data

[63] Continuation-in-part of Ser. No. 234,514, Feb. 17, 1981, Pat. No. 4,337,208.

[51] Int. Cl.$^3$ .......................... C07F 1/08; C07F 15/04; C07F 15/06; C11C 1/00
[52] U.S. Cl. ..................... 260/414; 260/413; 260/429 R; 260/429.3; 260/429.7; 260/429.9; 260/435 R; 260/438.1; 260/438.5 R; 260/439 R; 260/446; 260/447; 260/448 R
[58] Field of Search ................ 260/413 S, 414, 429 R, 260/429.3, 429.7, 429.9, 435 R, 438.1, 438.5 R, 439 R, 446, 447, 448 R

[56] References Cited

U.S. PATENT DOCUMENTS

| | | | |
|---|---|---|---|
| 2,573,049 | 10/1951 | Olson | 260/413 S |
| 2,650,932 | 9/1953 | Kebrich | 260/413 S |
| 2,753,364 | 7/1956 | Boner et al. | 260/413 S |
| 3,476,786 | 11/1969 | Lally et al. | 260/413 S |
| 4,218,385 | 8/1980 | Pike | 260/414 |
| 4,337,209 | 6/1982 | Akers et al. | 260/414 X |

FOREIGN PATENT DOCUMENTS

| | | | |
|---|---|---|---|
| 891858 | 3/1962 | United Kingdom | 260/414 |

*Primary Examiner*—Charles F. Warren
*Assistant Examiner*—E. M. Peters
*Attorney, Agent, or Firm*—James P. Scullin

[57] ABSTRACT

Oil-soluble metal salts are produced by the reaction of a polyvalent metal, such as nickel or cobalt, with an organic monocarboxylic acid in the presence of an alkali metal salt catalyst, water, oxygen, and an inert, water-immiscible organic solvent.

10 Claims, No Drawings

PROCESS FOR THE PRODUCTION OF OIL-SOLUBLE METAL SALTS

This is a continuation-in-part of my copending application Ser. No. 234,514, which was filed on Feb. 17, 1981, now U.S. Pat. No. 4,337,208.

This invention relates to a process for the production of oil-soluble metal salts. More particularly, it relates to a process for the production of metal salts by direct metal reaction using a catalyst that comprises an alkali metal salt.

Oil-soluble metal salts are widely used as paint, varnish, and printing ink driers, as lubricant additives, as catalysts for the chemical industry, and as fuel oil additives. These metal salts are produced either by double decomposition processes employing a water-soluble salt of the metal and an alkali metal salt of an organic monocarboxylic acid, by the fusion of an organic monocarboxylic acid with the oxide, hydroxide, carbonate, acetate, or other suitable compound of the metal, or by the direct reaction of the metal with an organic monocarboxylic acid (DMR process).

The double decomposition processes and the fusion processes have disadvantages that limit their use in the commercial production of oil-soluble metal salts of organic acids. The double decomposition processes require the use of relatively costly water-soluble metal salts and complicated processing equipment, and they yield products that are contaminated with reaction by-products that must be removed before the metal salts can be used in most applications. The fusion processes, which are more direct and less costly to carry out than the double decomposition processes, cannot be practiced with all of the polyvalent metals. In addition, some of these processes are not economical because the cost of the metal content of the metal compounds that are used in them is higher than that of the metal itself. The processes involving the direct metal reaction for the production of oil-soluble metal salts that have been disclosed in the prior art usually call for heating a metal with an organic monocarboxylic acid in the presence of water and oxygen. When carried out in the presence of a catalyst, such as a lower aliphatic acid, sulfuric acid, and/or a metal halide, these processes, when used to produce oil-soluble salts of nickel, cobalt, and other corrosion-resistant metals, require very long reaction periods and/or the use of large amounts of water and/or glycols or glycol ethers to produce commercially-useful products.

In copending application U.S. Ser. No. 234,514, U.S. Pat. No. 4,337,208, which is incorporated herein by reference, I disclosed that when the catalyst used in the production of oil-soluble metal salts by the direct reaction of a polyvalent metal with an organic monocarboxylic acid is an ammonium salt it is possible to produce efficiently oil-soluble salts of nickel, cobalt, and other corrosion-resistant metals that cannot be prepared by the previously-known direct metal reaction processes. The use of an ammonium salt catalyst also provides excellent yields of oil-soluble salts of other metals in reaction times that are considerably shorter than those of the direct metal reaction processes of the art. Unlike products prepared by the previously-known DMR processes that contain as much as 25% by weight of free organic acid, nickel salt solutions and other metal salt solutions prepared by the DMR process that uses an ammonium salt catalyst contain little or no free organic acid.

While the process of copending application U.S. Ser No. 234,514, U.S. Pat. No. 4,337,208, produces oil-soluble metal salts efficiently and economically, it cannot be used when the metal salts are to be employed in applications in which the presence of small amounts of ammonium salts has a deleterious effect on their properties. For example, when the metal salts are used as catalysts in dimerization processes and certain other chemical processes, their activity is inhibited by the small amounts of ammonium salts that are present in metal salts prepared by the DMR process that uses ammonium salt catalysts.

In accordance with this invention, it has been found that in direct metal reaction processes for the production of oil-soluble polyvalent metal salts catalysts that comprise alkali metal salts are as efficient and as economical as the ammonium salt catalysts disclosed in U.S. Ser. No. 234,514, U.S. Pat. No. 4,337,208, and that metal salts prepared in the presence of alkali metal salt catalysts do not contain amounts of residual catalyst or other impurities that will have an adverse effect on their activity as catalysts in various chemical processes.

In the process of this invention, oil-soluble salts of polyvalent metals are prepared rapidly and efficiently by heating a polyvalent metal with an orgaic monocarboxylic acid in the presence of water, oxygen, an inert water-immiscible organic solvent, and a catalyst that comprises an alkali metal metal salt until substantially all of the metal has reacted.

While the process of this invention is of particular value in the preparation of salts of metals that are very resistant to corrosion, such as nickel and cobalt, that cannot be prepared efficiently by most of the previously-known direct metal reaction processes, it can also be used to produce oil-soluble salts of polyvalent metals that are ordinarily classified as corrosion resistant, for example, aluminum, strontium, copper, iron, cadmium, zirconium, bismuth, chromium, lead, manganese, antimony, zinc, tin, and molybdenum, as well as those that are less resistant to reaction with organic acids. A single polyvalent metal or a combination of two or more of these metals may be used in the process of this invention.

The metal is usually used in the form of powder, granules, wire, shavings, or the like so that a large metal surface is exposed to the acid and the conversion of the metal to its salt is readily accomplished.

A wide variety of organic monocarboxylic acids can be used in the process of this invention. They include aliphatic acids, cycloaliphatic acids, aromatic acids, and mixtures of these acids. The preferred monocarboxylic acids are saturated and unsaturated aliphatic and cycloaliphatic monocarboxylic acids having from 5 to 18 carbon atoms. Examples of these preferred acids include n-pentanoic acid, 2-methylbutanoic acid, n-hexanoic acid, 2-ethylbutanoic acid, n-heptanoic acid, n-octanoic acid, 2-ethylhexanoic acid, 2-ethyl-4-methylpentanoic acid, n-nonanoic acid, neononanoic acids, isononanoic acids, 2-methylnonanoic acid, 2-ethyloctanoic acid, n-decanoic acid, neodecanoic acid, dodecanoic acid, tetradecanoic acid, octadecanoic acid, 2-ethyl-3-propylacrylic acid, octenoic acid, 10-undecenoic acid, oleic acid, naphthenic acids, rosin acids, and terpene acids. A single monocarboxylic acid or a mixture of these acids can be used in the process of this invention. Commercially-available mixtures of acids that can be used include tall oil fatty acids, linseed oil fatty acids and other drying oil and semi-drying oil fatty acids, $C_{8-18}$ OXO acids, and $C_{9-11}$ trialkylacetic acids.

Equivalent amounts of the metal and the organic monocarboxylic acid or a stoichiometric excess of either metal or acid may be used in this process. It is generally preferred that a 0.1% to 50% molar excess of the monocarboxylic acid be used.

In the process of this invention, the reaction of the polyvalent metal and organic monocarboxylic acid is carried out in the presence of a catalyst that comprises an alkali metal salt that is preferably a sodium salt, a potassium salt, or a mixture thereof. Alkali metal salts that can be used in the process include salts of mineral acids, salts of monocarboxylic acids having 1 to 4 carbon atoms, or mixtures of these salts. The catalyst is preferably a mixture that contains 10% to 90% by weight of at least one alkali metal salt of a mineral acid, such as sodium nitrate, sodium sulfate, sodium phosphate, sodium chloride, sodium fluoride, sodium carbonate, potassium nitrate, potassium phosphate, potassium carbonate, potassium chlorate, lithium nitrate, lithium chloride, lithium flouride, and lithium chlorate, and 10% to 90% by weight of at least one alkali metal salt of an aliphatic monocarboxylic acid, such as sodium formate, sodium acetate, sodium propionate, sodium butyrate, potassium formate, potassium acetate, potassium isopropionate, potassium butyrate, lithium formate, lithium acetate, and lithium isobutyrate. Particularly advantageous results have been obtained using a mixture that contains 30% to 70% by weight of an alkali metal salt of a mineral acid and 30% to 70% by weight of an alkali metal salt of a monocarboxylic acid having 1 to 4 carbon atoms.

In a preferred embodiment of the invention, the catalyst that is used in the production of oil-soluble polyvalent metal salts of organic monocarboxylic acids is a mixture comprising 30% to 70% by weight of an alkali metal salt component as hereinbefore defined and 30% to 70% by weight of an ammonium salt component that is an ammonium salt of a mineral acid, an ammonium salt of a monocarboxylic acid, or a mixture thereof. Especially good results have been obtained using a catalyst that contained about 50% by weight of an alkali metal salt of a monocarboxylic acid and about 50% by weight of an ammonium salt of a mineral acid.

The amount of the catalyst that is used is that which will bring about the desired reduction in the time required for the polyvalent metal to react with the monocarboxylic acid to form the oil-soluble metal salt. It is dependent upon such factors as the choice of polyvalent metal, monocarboxylic acid, and catalyst components and the reaction conditions employed. When the catalyst is a mixture of an alkali metal salt and an ammonium salt, the relative amounts of the alkali metal salt and the ammonium salt in the catalyst and the amount of the catalyst that is used must be those that will yield a polyvalent metal salt that contains an amount of ammonium salt that will not interfere with the subsequent use of the polyvalent metal salt. In most cases the amount of the alkali metal salt catalyst used is not more than 75% of the weight of metal in the reaction mixture.

In the process of this invention, the reaction between the polyvalent metal and the monocarboxylic acid is carried out in the presence of a catalyst that comprises an alkali metal salt, water, oxygen, and an inert, water-immiscible organic solvent. The water does not take part in the reaction; it merely assists in distributing the catalyst uniformly throughout the reaction mixture. Water may be added to the reaction mixture before, during, or after the addition of the catalyst, or an aqueous solution of the catalyst may be added to the reaction mixture. The amount of water that is added is between about 20% and 80% of the weight of the metal, preferably between 40% and 60% of the weight of the metal.

Oxygen may be added to the reaction mixture as such or as a compound, for example, a peroxide, that will react under the reaction conditions to release oxygen. The addition of oxygen is usually accomplished by bubbling an oxygen-containing gas through the mixture during the reaction. The amount of oxygen that is added can be varied within wide limits. In most cases, air is bubbled through the reaction mixture at such a rate that a total of about 2 moles to 100 moles of oxygen is provided per mole of metal.

The preparation of the oil-soluble metal salts by the process of this invention is carried out in the presence of an inert, water-immiscible, organic solvent that is preferably an aliphatic or aromatic hydrocarbon or chlorinated hydrocarbon. Suitable solvents include such hydrocarbons as benzene, toluene, xylene, ethylbenzene, dipentene, turpentine, petroleum hydrocarbon fractions such as gasoline, mineral spirits, kerosene, mineral oil, fuel oil, and aromatic naphthas and such chlorinated hydrocarbons as carbon tetrachloride, o-dichlorobenzene, monochlorotoluene, ethylene dichloride, and perchloroethylene. If desired, mixtures of these solvents can be used.

This process for the production of oil-soluble polyvalent metal salts of organic monocarboxylic acids may be carried out under either atmospheric pressure or superatmospheric pressures. Although the rate of reaction is increased at superatmospheric pressures, it is usually more economical and more convenient to prepare the metal salts at atmospheric pressure. Reaction temperatures in the range of 70° C. to 150° C. may be used. Optimum results have been obtained when the reaction was carried out at a temperature in the range of 80° C. to 100° C.

The reaction between polyvalent metal and the organic monocarboxylic acid in the presence of an alkali metal salt catalyst, water, an inert organic solvent, and oxygen is continued until substantially no unreacted metal remains in the reaction mixture or until the acid number of the reaction mixture has reached the desired level. When the reaction has been completed, the reaction mixture is heated to remove water from it and filtered to remove any insoluble materials that it contains. The product, which is a solution of a polyvalent metal salt of an organic monocarboxylic acid in an inert water-immiscible, organic solvent, contains from about 3% to 36% by weight of the metal. It can be used without purification or treatment other than the adjustment of its metal content to the desired level in any of the applications in which these polyvalent metal salts are commonly used.

The invention is further illustrated by the following examples.

EXAMPLE 1

A mixture of 50 grams (0.852 mole) of powdered nickel (particle size 3 to 7 microns), 250 grams (1.724 moles) of 2-ethylhexanoic acid (acid number, 387), a catalyst solution prepared by dissolving 10 grams of sodium nitrate in 25 grams of water, and 170 grams of mineral spirits was agitated and heated to 95° C. The reaction mixture was maintained at 90°–95° C. for 16 hours while it was sparged with air at the rate of 30 liters per hour. It was then heated to 135° C. under vacuum to remove water from it. After the reaction product had been filtered and diluted with mineral spirits, there was obtained a solution of nickel 2-ethylhexanoate in mineral spirits that contained 10% by weight of nickel and had an acid number of 39.

EXAMPLE 2

When the procedure described in Example 1 was repeated except that the catalyst was a solution of 10 grams of potassium nitrate in 25 grams of water, a reaction period of 16 hours was required to produce a nickel 2-ethylhexanoate solution that contained 10% nickel and had an acid number of 37.

EXAMPLE 3

The procedure described in Example 1 was repeated except that the catalyst was a solution of 10 grams of potassium nitrate and 5 grams of sodium formate in 42.5 grams of water. A reaction period of 16 hours was required to produce the nickel 2-ethylhexanoate solution. The solution, which was diluted to 10% metal content with mineral spirits, had an acid number of 20.

COMPARATIVE EXAMPLE A

When the procedure described in Example 1 was repeated except that an alkali metal salt catalyst was not used, only slight reaction between the nickel and 2-ethylhexanoic acid occurred in a 20-hour heating period at 95° C.

EXAMPLE 4

A mixture of 50 grams of cobalt powder, 316.2 grams (1.697 moles) of neodecanoic acid (acid number, 301), a catalyst solution prepared by dissolving 2.5 grams of sodium formate and 2.5 grams of ammonium nitrate in 20 grams of water, and 130 grams of mineral spirits was heated to 85° C. and maintained at that temperature for 3.5 hours while it was sparged with air at the rate of 30 liters per hour. After the addition of a solution prepared by dissolving 2.5 grams of sodium formate and 2.5 grams of ammonium nitrate in 20 grams of water, the reaction mixture was heated at 85° C. for 2.5 hours. It was then heated at 135° C., under vacuum to remove water from it, filtered, and diluted with mineral spirits. There was obtained a solution of cobalt neodecanoate in mineral spirits that contained 10% by weight of cobalt and had an acid number of 16.

EXAMPLE 5

A mixture of 50 grams of cobalt powder, 316.2 grams (1.697 moles) of neodecanoic acid (acid number, 301), a catalyst solution prepared by dissolving 5 grams of sodium formate and 5 grams of ammonium nitrate in 30 grams of water, and 130 grams of mineral spirits was heated at 85° C. for 7 hours while it was sparged with air at the rate of 30 liters per hour. The reaction mixture was heated at 135° C. under vacuum to remove water from it, filtered, and diluted with mineral spirits. There was obtained a solution of cobalt neodecanoate in mineral spirits that contained 10% cobalt and had an acid number of 18.

COMPARATIVE EXAMPLE B

When the procedure described in Example 5 was repeated except that an alkali metal salt catalyst was not used, a reaction period of 10 hours was required to produce the cobalt salt solution.

EXAMPLE 6

A mixture of 60.3 grams (0.944 mole) of powdered copper (99.5% Cu; particle size, less than 45 microns), 150 grams (1.034 moles) of 2-ethylhexanoic acid, 150 grams (1.034 moles) of isooctanoic acid, 140 grams of mineral spirits, 2.5 grams of sodium nitrate, 5.0 grams of ammonium acetate, and 20 grams of water was agitated and heated to 95° C. The reaction mixture was maintained at 95° C. for 13.5 hours while it was sparged with air at the rate of 30 liters per hour. It was then heated to 135° C. under vacuum to remove water from it. After the reaction product had been filtered and diluted with mineral spirits, there was obtained a solution of copper salts of 2-ethylhexanoic acid and isooctanoic acid in mineral spirits that contained 12% by weight of copper and had an acid number of 16.7. A 95.5% yield of the copper salts was obtained.

EXAMPLE 7

A mixture of 60.3 grams (0.944 mole) of powdered copper (99.5% Cu; particle size, less than 45 microns), 150 grams (1.034 moles) of 2-ethylhexanoic acid, 150 grams (1.034 moles) of isooctanoic acid, 140 grams of mineral spirits, 2.5 grams of potassium nitrate, 2.5 grams of ammonium formate, and 20 grams of water was agitated and heated to 95° C. The reaction mixture was maintained at 95° C. for 12 hours while it was sparged with air at the rate of 30 liters per hour. It was then dried under vacuum at 135° C. and filtered. After the reaction product had been diluted with mineral spirits, there was obtained a solution of copper salts of 2-ethylhexanoic acid and isooctanoic acid in mineral spirits that contained 11.6% by weight of copper and had an acid number of 26. A 91.5% yield of the copper salts was obtained.

COMPARATIVE EXAMPLE C

When the procedure described in Example 6 was repeated except that a catalyst was not used, an 87% yield of the copper salts was obtained after a 24-hour reaction period.

Each of the other polyvalent metal salts disclosed herein can also be prepared efficiently by the DMR process using an alkali metal salt catalyst.

What is claimed is:

1. In the process for the production of oil-soluble metal salts wherein a reaction mixture that comprises a polyvalent metal, an organic monocarboxylic acid having 5 to 18 carbon atoms, water, and an inert, water-immiscible organic solvent is heated in the presence of oxygen for a period of time sufficient to form the metal salt of said monocarboxylic acid, the improvement wherein the reaction between the polyvalent metal and the monocarboxylic acid is carried out in the presence of an alkali metal salt catalyst.

2. The process of claim 1 wherein the alkali metal salt catalyst is selected from the group consisting of sodium salts of mineral acids, sodium salts of organic monocarboxylic acids having 1 to 4 carbon atoms, potassium salts of mineral acids, potassium salts of organic monocarboxylic acids having 1 to 4 carbon atoms, and mixtures thereof.

3. The process of claim 1 wherein the alkali metal salt catalyst is a mixture containing 10% to 90% by weight of an alkali metal salt of a mineral acid and 10% to 90% by weight of an alkali metal salt of a monocarboxylic acid having 1 to 4 carbon atoms.

4. The process of claim 1 wherein the alkali metal salt catalyst comprises an alkali metal nitrate.

5. The process of claim 1 wherein the alkali metal salt catalyst comprises an alkali metal nitrate and an alklai metal salt of a monocarboxylic acid having 1 to 4 carbon atoms.

6. The process of claim 1 wherein the alkali metal catalyst comprises 30% to 70% by weight of an alkali metal salt component selected from the group consisting of alkali metal salts of mineral acids, alkali metal salts of monocarboxylic acids having 1 to 4 carbon atoms, and mixtures thereof and 30% to 70% by weight of an ammonium salt component selected from the group consisting of ammonium salts of mineral acids, ammonium salts of monocarboxylic acids having 1 to 4 carbon atoms, and mixtures thereof.

7. The process of claim 6 wherein the alkali metal catalyst comprises an alkali metal salt of a monocarboxylic acid having 1 to 4 carbon atoms and an ammonium salt of a mineral acid.

8. The process of claim 6 wherein the alkali metal catalyst comprises an alkali metal salt of a mineral acid and an ammonium salt of a monocarboxylic acid having 1 to 4 carbon atoms.

9. The process of claim 6 wherein the alkali metal catalyst comprises an alkali metal formate and ammonium nitrate.

10. The process of claim 6 wherein the alkali metal catalyst comprises an alkali metal nitrate and ammonium acetate.

* * * * *